(12) United States Patent
Lee

(10) Patent No.: US 9,855,016 B2
(45) Date of Patent: Jan. 2, 2018

(54) RADIATION IMAGING APPARATUS

(71) Applicant: Samsung Electronics Co., Ltd., Gyeonggi-do (KR)

(72) Inventor: Jeong-pil Lee, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 80 days.

(21) Appl. No.: 14/876,136

(22) Filed: Oct. 6, 2015

(65) Prior Publication Data
US 2016/0220203 A1 Aug. 4, 2016

(30) Foreign Application Priority Data
Feb. 3, 2015 (KR) .................. 10-2015-0016728

(51) Int. Cl.
*A61B 6/00* (2006.01)

(52) U.S. Cl.
CPC .......... *A61B 6/4441* (2013.01); *A61B 6/4014* (2013.01); *A61B 6/4464* (2013.01)

(58) Field of Classification Search
CPC ........................... A61B 6/4014; A61B 6/4464
See application file for complete search history.

(56) References Cited

U.S. PATENT DOCUMENTS 5,095,501 A * 3/1992 Kobayashi ........... A61B 6/4441
378/192
6,104,780 A * 8/2000 Hanover ............. A61B 6/4014
378/101

\* cited by examiner

*Primary Examiner* — Dani Fox
(74) *Attorney, Agent, or Firm* — Cha + Reiter, LLC.

(57) ABSTRACT

Provided is a radiation imaging apparatus including a moving member configured to move along a ceiling; a first arm supported by the moving member to rotate with respect to a first rotation axis, wherein the first arm supports a first radiation source and a first radiation detector which are facing each other; a second arm configured to rotate with respect to a second rotation axis crossing the first rotation axis, wherein the second ram supports a second radiation source and a second radiation detector which are facing each other; and a supporting arm supported by the moving member, wherein the supporting arm supports the second arm such that the second arm may be rotatable with respect to the second rotation axis.

12 Claims, 13 Drawing Sheets

RADIATION IMAGING APPARATUS

CLAIM OF PRIORITY

This application claims the benefit of Korean Patent Application No. 10-2015-0016728, filed on Feb. 3, 2015, in the Korean Intellectual Property Office, the disclosure of which is incorporated herein in its entirety by reference.

BACKGROUND

The present disclosure relates to a bi-plane radiation imaging apparatus.

A radiation imaging apparatus can include various imaging modes such as an X-rays, computerized tomography (CT), ultrasound, electronic beam tomography, and a magnetic resonance imaging.

A radiation imaging apparatus can include a radiation source and a radiation detector that are disposed to face each other. Radiation irradiated from the radiation source passes through a patient and reaches the radiation detector. The radiation detector detects variable attenuation of received radiation to generate an image.

A radiation imaging apparatus may be classified into a single plane radiation imaging apparatus or a bi plane radiation imaging apparatus, depending on the obtained images. The single plane radiation imaging apparatus produces a two dimensional image by using a single radiation source and a single radiation detector. The bi-plane radiation imaging apparatus produces a three dimensional image by using a plurality of radiation sources and a plurality of radiation detectors.

As the bi-plane radiation imaging apparatus produces three dimensional images, the apparatus may be used in medical fields where there is a need of precise treatment, e.g., cerebrovascular surgery.

SUMMARY

Provided is a radiation imaging apparatus that may generate a three dimensional image and allow simultaneous movement of first and second arms, in which a radiation source and a radiation detector are supported by either the first arm or the second arm.

Additional aspects will be set forth in part in the description which follows and, in part, will be apparent from the description, or may be learned by practice of the presented embodiments.

According to an aspect of an embodiment, a radiation imaging apparatus includes a moving member configured to move along a ceiling; a first arm supported by the moving member to rotate with respect to a first rotation axis, wherein the first arm supports a first radiation source and a first radiation detector which are facing each other; a second arm configured to rotate with respect to a second rotation axis crossing the first rotation axis, wherein the second arm supports a second radiation source and a second radiation detector which are facing each other; and a supporting arm supported by the moving member, wherein the supporting arm supports the second arm such that the second arm is rotatable with respect to the second rotation axis.

The supporting arm may be supported by the moving member to rotate with respect to the first rotation axis.

At least one arm of the first arm and the second arm may be spaced apart from a plane defined by a virtual line connecting a radiation source to a radiation detector supported by the at least one arm and a rotation axis of the at least one arm.

The second arm may be spaced apart from a plane defined by a virtual line connecting the second radiation source to the second radiation detector and the second rotation axis.

A point where the first rotation axis and the second rotation axis intersect may correspond to a point where a virtual line connecting the first radiation source to the first radiation detector and the virtual line connecting the second radiation source to the second radiation detector intersect.

Each of the first and second arms is arc shaped.

The first arm may be supported by the moving member through a first rotation member rotatably provided on the moving member, and the second arm may be supported by the supporting arm through a second rotation member rotatably provided on the supporting arm.

The first arm may be configured to slide along the first rotation member.

The second arm may be configured to slide along the second rotation member.

The supporting arm may be arc shaped, and the second rotation member may be configured to slide along the supporting arm.

An extension direction of the first rotation axis may be perpendicular to a movement direction of the moving member.

The moving member may be configured to move along a length direction of an examination table.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
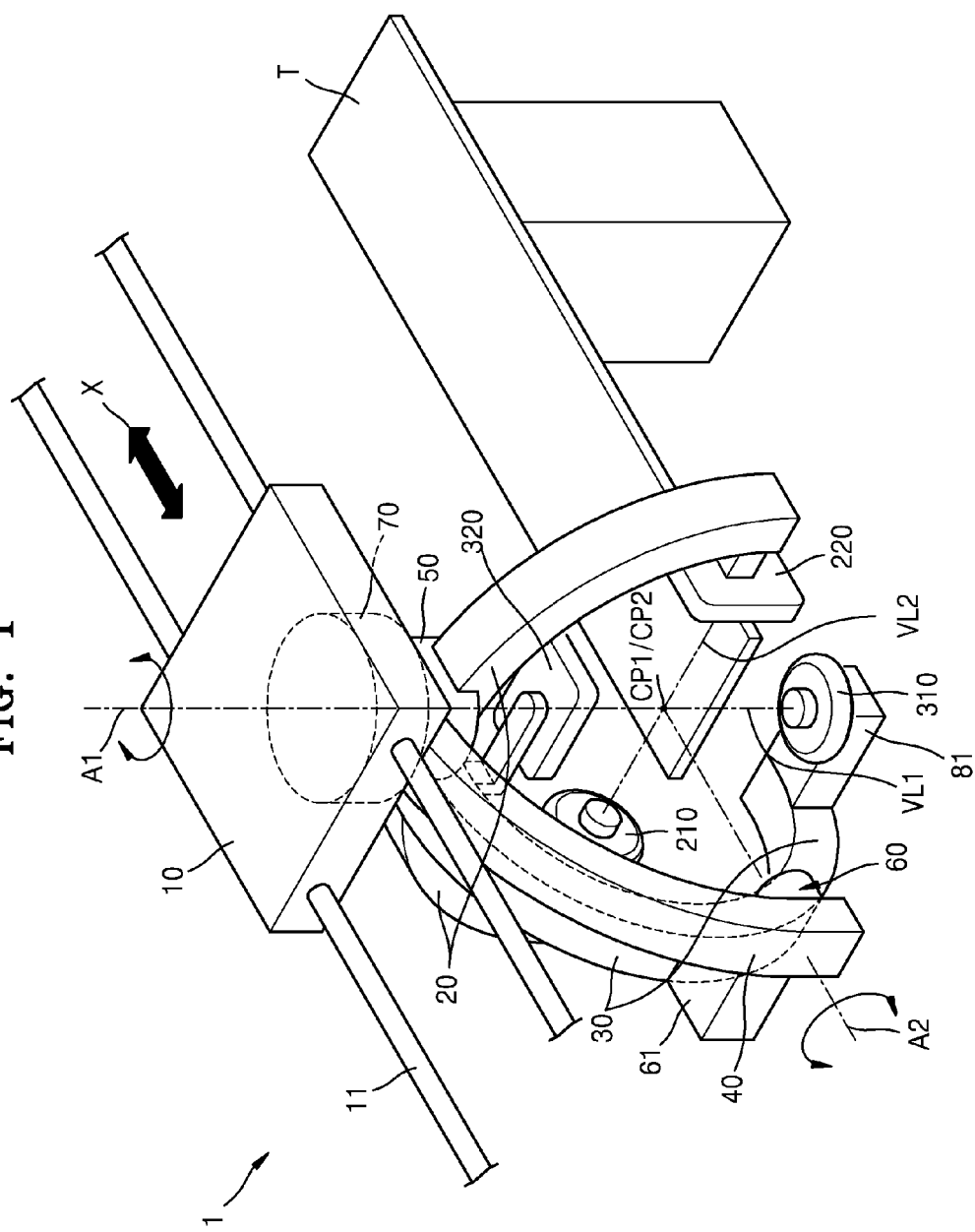
FIG. 1 is a perspective view conceptually illustrating a radiation imaging apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, a configuration and an operation of a radiation imaging apparatus according to embodiments thereof will be described in detail with reference to the accompanying drawings. In the following embodiments, it will be understood that although the terms first, second, and third are used herein to describe various elements, these elements should not be limited by these terms. These terms are only used to distinguish one element from another element.

Figure 2A:
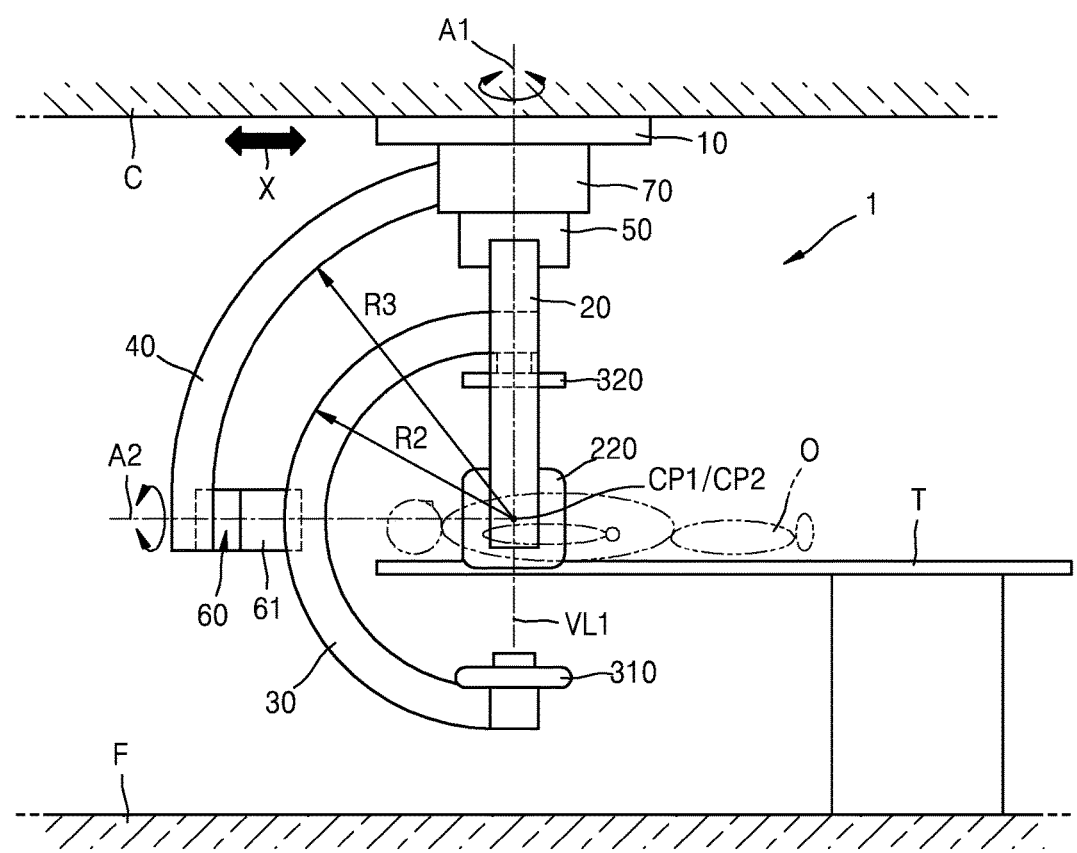
FIG. 2A and FIG. 2B are each a side view and a front view of the radiation imaging apparatus according to an embodiment.

FIG. 1 is a perspective view illustrating a radiation imaging apparatus 1 according to an embodiment. FIG. 2A is a side view and FIG. 2B is a front view of the radiation imaging apparatus 1 according to an embodiment.

Figure 2B:
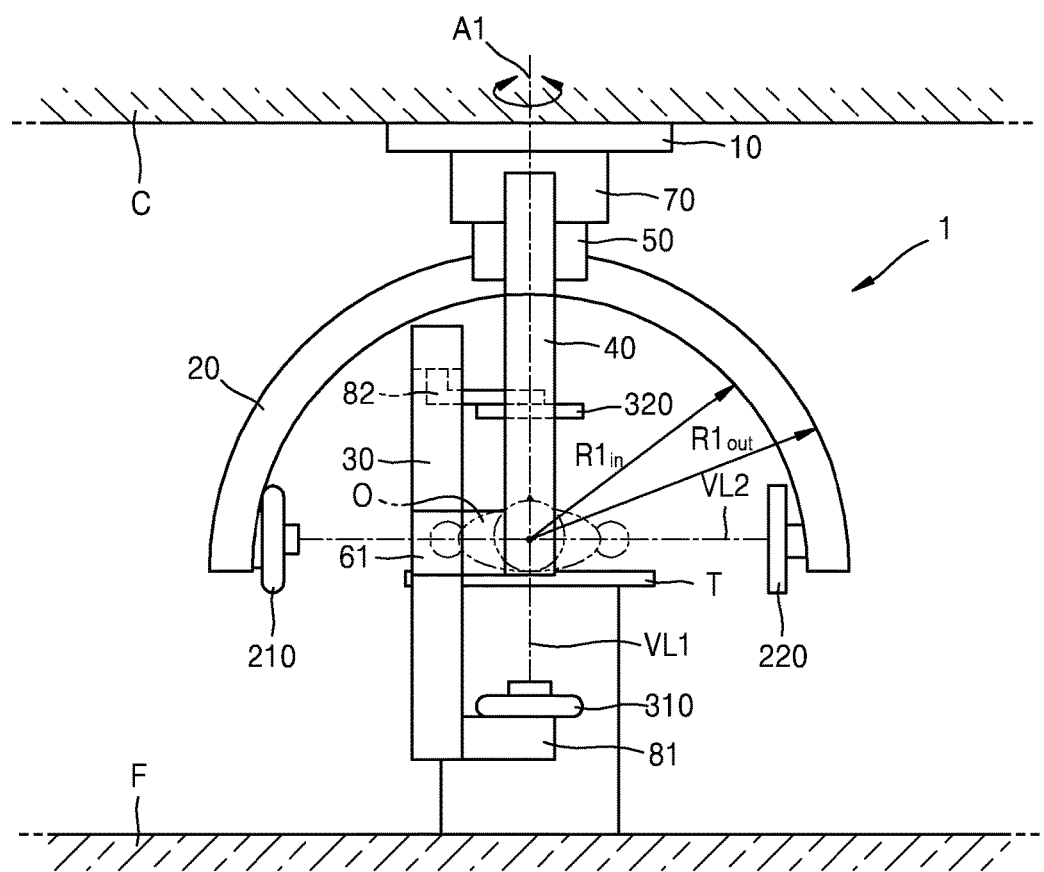

Referring to FIGS. 1, 2A, and 2B, the radiation imaging apparatus 1 may include a moving member 10, first arm 20, second arm 30, and a supporting arm 40 provided (or installed) on the moving member 10.

The moving member 10 may move along a ceiling C. Movement of the moving member 10 along the ceiling C, for example, via a guide rail 11, may overcome movement limitations of the moving member 10 or a user due to an examination table T, compared to when a moving member is fixedly disposed on a floor F.

The moving member 10 may move along a length direction X of the examination table T. However, a movement direction of the moving member 10 is not limited thereto. For example, the moving member 10 may move along a direction intersecting the length direction X of the examination table T.

The moving member 10 may move along the ceiling C by sliding. For example, the moving member 10 may move along the guide rail 11 fixedly disposed on the ceiling C. However, a moving method of the moving member 10 is not limited thereto, and one or more suitable methods may be available.

The first arm 20 may be rotatably supported by the moving member 10. For example, the first arm 20 may be supported through a first rotation member 50 that is rotatably connected to the moving member 10.

The first arm 20 may support the first radiation source 210 and the first radiation detector 220 which are facing each other. The first arm 20 may be an arc shaped. For example, the first arm 20 may be C-shaped, or substantially 180 degrees semicircular. The first radiation source 210 and the first radiation detector 220 may be supported by each end of the first arm 20. The first radiation source 210 and the first radiation detector 220 may be used to capture a frontal view.

Radiation irradiated from the first radiation source 210 may pass through an object O (shown in FIG. 2) on the examination table T and reach the first radiation detector 220. The first radiation detector 220 detects variable attenuation of received radiation to generate an image. The radiation irradiated from the first radiation source 210 may be any one of X-rays, ultrasound, magnetic fields, and/or pulses of radio wave energy.

The first arm 20 may rotate with respect to a first rotation axis A1 about the moving member 10. The first rotation axis A1 may be perpendicular or orthogonal to a movement direction X of the moving member 10.

The second arm 30 may rotate with respect to a second rotation axis A2 intersecting the first rotation axis A1. The second arm 30 may support the second radiation source 310 and the second radiation detector 320 which are facing each other.

The second arm 30 may be arc shaped. For example, the second arm 30 may be a C-shaped, or substantially 180 degrees semicircular. The second radiation source 310 and the second radiation detector 320 may be supported by each end of the second arm 30. The second radiation source 310 and the second radiation detector 320 may be used to capture a lateral view.

The first rotation axis A1 and the second rotation axis A2 may intersect. For example, the first rotation axis A1 and the second rotation axis A2 may intersect at 90°. A first intersection point CP1 may be the point where the first rotation axis A1 intersects the second rotation axis A2.

A virtual line VL2 connecting the first radiation source 210 to the first radiation detector 220 and a virtual line VL1 connecting the second radiation source 310 to the second radiation detector 320 may intersect. In this regard, a virtual line VL connecting a radiation source to a radiation detector may be defined as the shortest straight line connecting the radiation source to the radiation detector. A second intersection point CP2 may be the point where the virtual lines VL intersect. The second intersection point CP2 may correspond to the first intersection point CP1 where the first and second rotation axes A1 and A2 intersect.

Radiation irradiated from the second radiation source 310 may pass through an object O on the examination table T and reach the second radiation detector 320. The second radiation detector 320 detects variable attenuation of received radiation to generate an image. The radiation irradiated from the second radiation source 310 may be X-rays, ultrasound, magnetic fields, and/or pulses of radio wave energy.

Based on detected information from the first and second radiation detectors 220 and 320, a three dimensional image may be obtained.

The second arm 30 may be supported by the moving member 10. For example, the second arm 30 may be rotatably supported by the moving member 10 through the supporting arm 40. The second arm 30 may be supported through a second rotation member 60 which is rotatably connected to the supporting arm 40. The second rotation member 60 may be rotatable with respect to the second rotation axis A2 about the supporting arm 40.

The supporting arm 40 may be rotatably supported by the moving member 10. For example, the supporting arm 40 may be supported through a third rotation member 70 which is rotatably connected to the moving member 10. The third rotation member 70 may be rotatable with respect to the first rotation axis A1 about the moving member 10.

As described above, the first arm 20 may be supported by the moving member 10, and the second arm 30 may be supported by the moving member 10 through the supporting arm 40. As such, as the first arm 20 and the second arm 30 may be supported by the moving member 10, the first arm 20 and the second arm 30 may simultaneously move with the moving member 10.

Figure 3A:
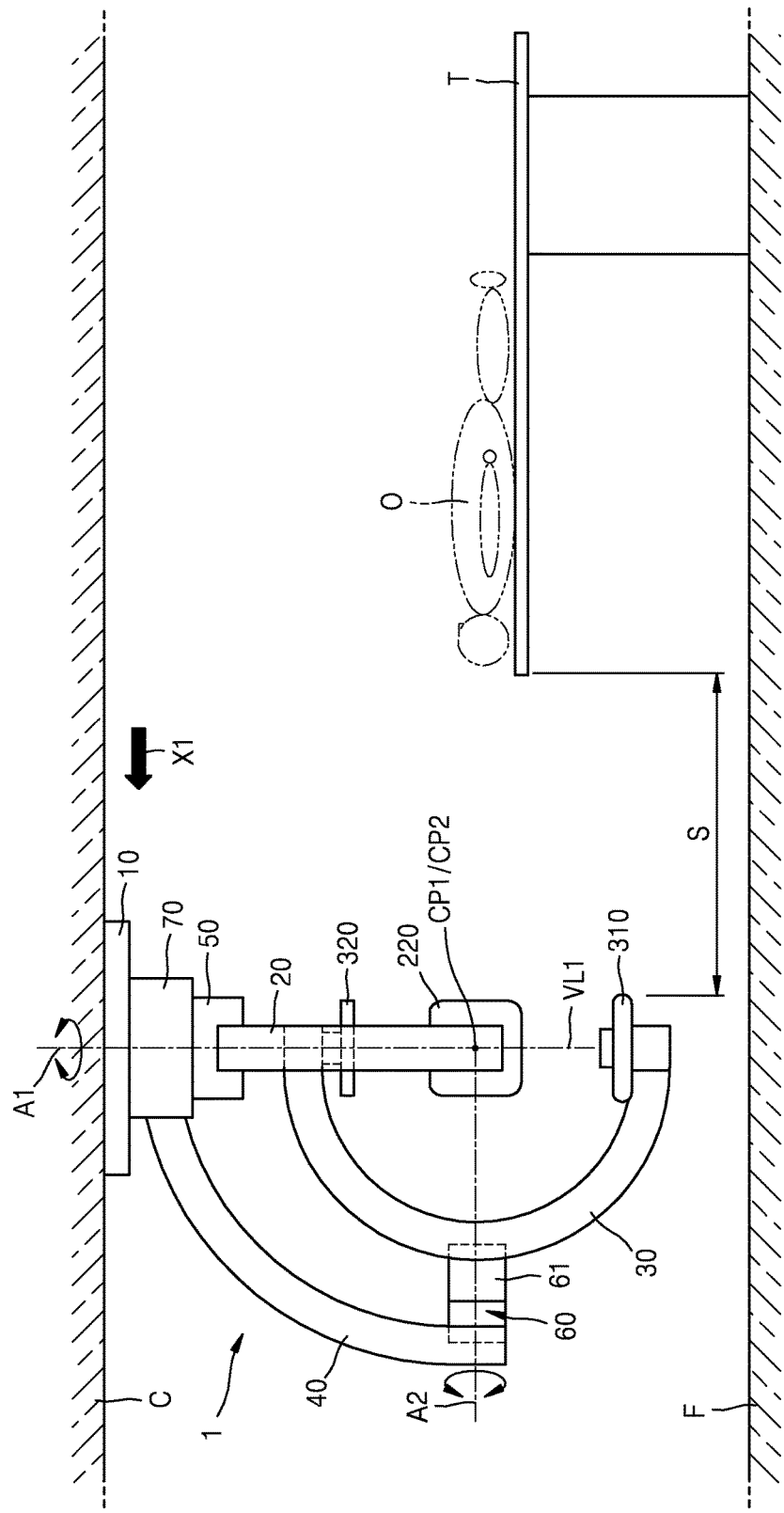
FIG. 3A and FIG. 3B are views illustrating movement of the radiation imaging apparatus including a first arm and a second arm due to movement of the moving member.
Figure 3B:
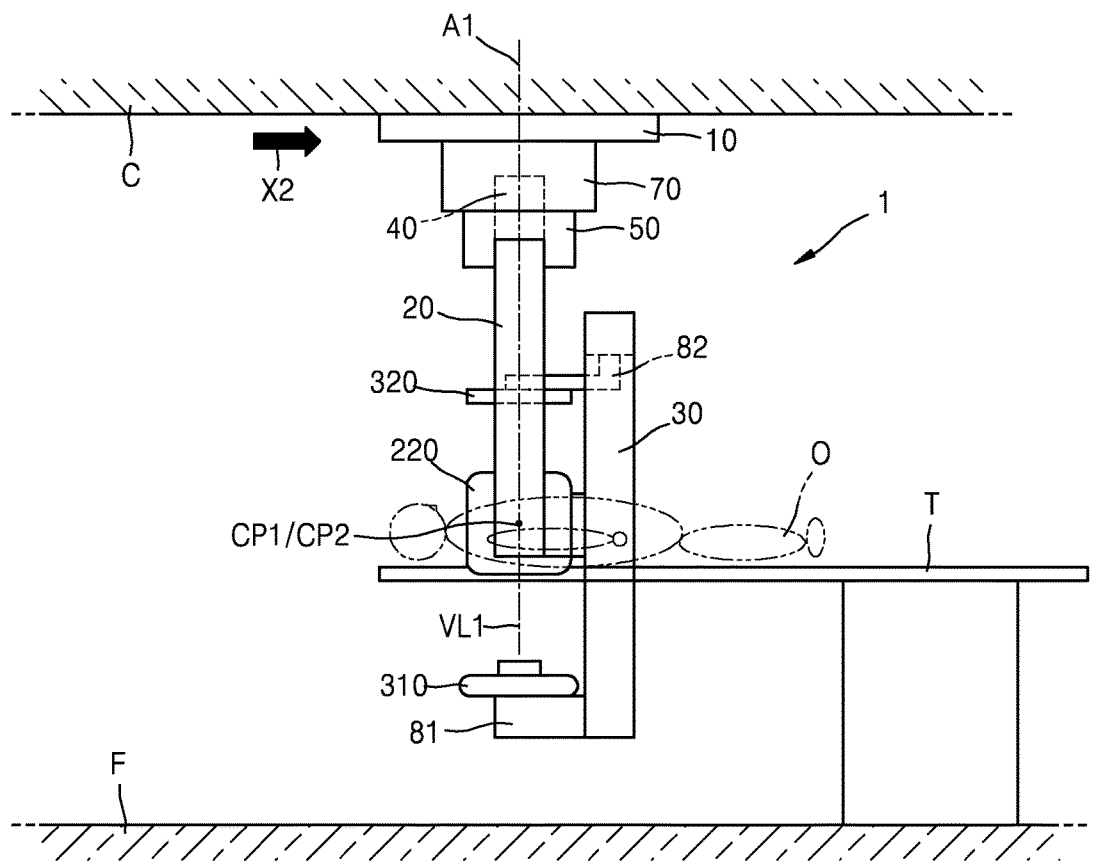

FIGS. 3A and 3B are views illustrating movement of the radiation imaging apparatus 1 including the first arm 20 and the second arm 30 due to the movement of the moving member 10. FIG. 3A schematically illustrates the radiation imaging apparatus 1 in FIG. 2A moves in a direction X1 farther S from the examination table T. FIG. 3B schematically illustrates when the radiation imaging apparatus 1 in FIG. 2A moves when the supporting arm 40 rotates 90 degrees.

Referring to FIG. 3A, the radiation imaging apparatus 1 may be moved by sliding the moving member 10 in a direction X1, away from the examination table T. For example, when the radiation imaging apparatus 1 is not being used, a user may move the moving member 10 of the radiation imaging apparatus 1, having the first and second arms 20 and 30 becoming farther from the examination table T. Accordingly, when the radiation imaging apparatus 1 does not need to be used, sufficient space S near the examination table T may be secured. In addition, as the first and second arms 20 and 30 may be simultaneously moved by the movement of the moving member 10, a collision between the first arm 20 and the second arm 30 which may occur due to independent movement of the first arm 20 and the second arm 30 may be prevented.

Referring to FIG. 3B, the radiation imaging apparatus 1 may be moved in the direction X2 becoming closer to the examination table T by the moving member 10. For example, when the radiation imaging apparatus 1 is to be used, a user may move the moving member 10, having the first and second arms 20 and 30 becoming closer to the examination table T.

In addition, even in the case that a portion of the radiation imaging apparatus 1 moves to a position over the examination table T, by moving the moving member 10 before or while using the radiation imaging apparatus 1, the first arm 20 and the second arm 30 may be placed at an exact location.

Unlike as described in the present disclosure, when the first arm 20 and the second arm 30 move independently, a collision between the first arm 20 and second arm 30 may occur, or at least a process of adjusting the positional relationship between the first arm 20 and the second arm 30 may be required.

However, the radiation imaging apparatus 1 according to the present disclosure, the first arm 20 and the second arm 30 are simultaneously moved by the moving member 10, even when the first arm 20 and the second arm 30 are moved, the first intersection point CP1 and the second intersection point CP2 may maintain the same point. In other words, when the first arm 20 and second arm 30 are being moved, a process of adjusting the positional relationship between the first arm 20 and the second arm 30 may be omitted.

Hereinafter a structure will be described, which is for preventing interference between the supporting arm 40, the first arm 20, and the second arm 30, when at least one of the supporting arm 40, the first arm 20, and the second arm 30 rotates in the radiation imaging apparatus 1 according to the present disclosure.

Figure 4A:
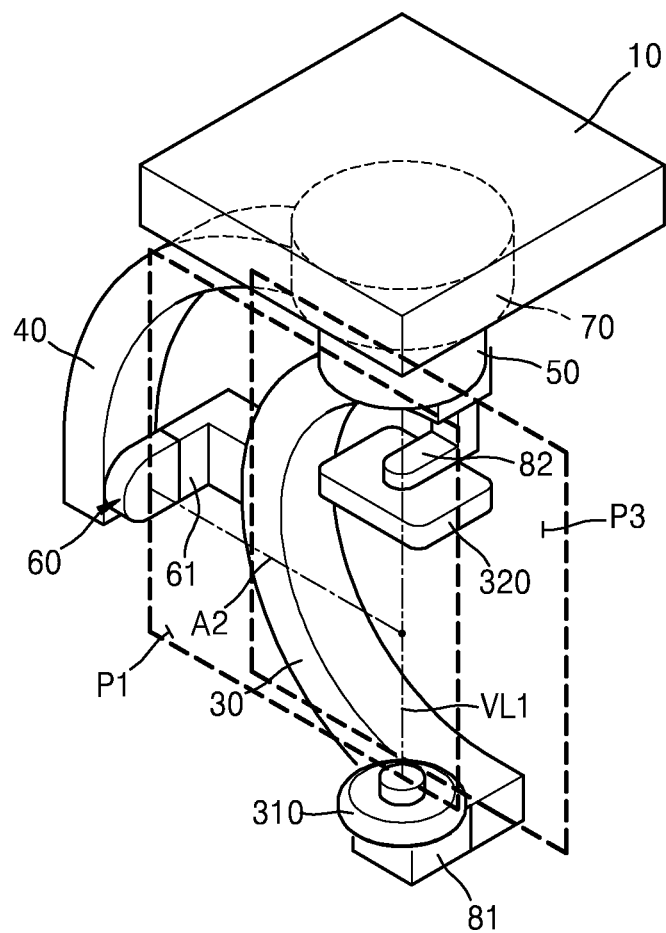
FIG. 4A and FIG. 4B are respectively a perspective view and a side view illustrating the radiation imaging apparatus according to an embodiment, focusing on the second arm.
Figure 4B:
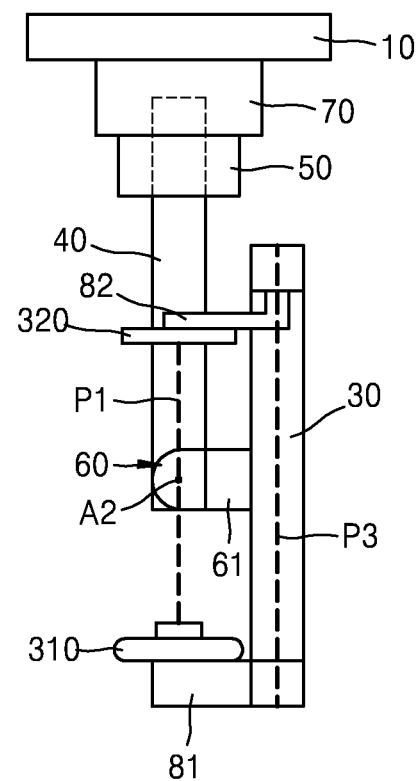

At least one arm of the first arm 20 and the second arm 30 may be spaced apart from a plane defined by a virtual line connecting a radiation source to a radiation detector supported by the arm and a rotation axis of the arm. For example, the second arm 30 may be spaced apart from a first plane P1 defined by the virtual line VL1 connecting the second radiation source 310 to the second radiation detector 320 and the second rotation axis A2 of the second arm 30. FIGS. 4A and 4B are respectively a perspective view and a side view illustrating the radiation imaging apparatus 1 according to the present disclosure, focusing on the second arm 30. In FIGS. 4A and 4B, the first arm 20 is not illustrated for convenience of description.

Referring to FIGS. 4A and 4B, the second arm 30 may be spaced apart from the first plane P1 defined by the virtual line VL1 connecting the second radiation source 310 to the second radiation detector 320 and the second rotation axis A2. The first plane P1 may be spaced apart from a plane P3 of the second arm 30.

A first connection link 61 may be between the second arm 30 and the supporting arm 40, and second connection links 81 and 82 may each be between the second arm 30 and the second radiation source 310 and between the second arm 30 and the second radiation detector 320. At least one portion of the first and second connection links 61, 81, and 82 may extend in a direction intersecting the second rotation axis A2. The first connection link 61 may be included in the second rotation member 60 and extend in a direction becoming farther from the second rotation axis A2. The second connection links 81 and 82 may extend from each of the ends of the second arm 30 in a direction becoming closer to the second rotation axis A2. By the first and second connection links 61, 81, and 82, the second arm 30 may be spaced apart from the virtual line VL1 connecting the second radiation source 310 to the second radiation detector 320 and the first plane P1 defined by the second rotation axis A2.

Figure 5:
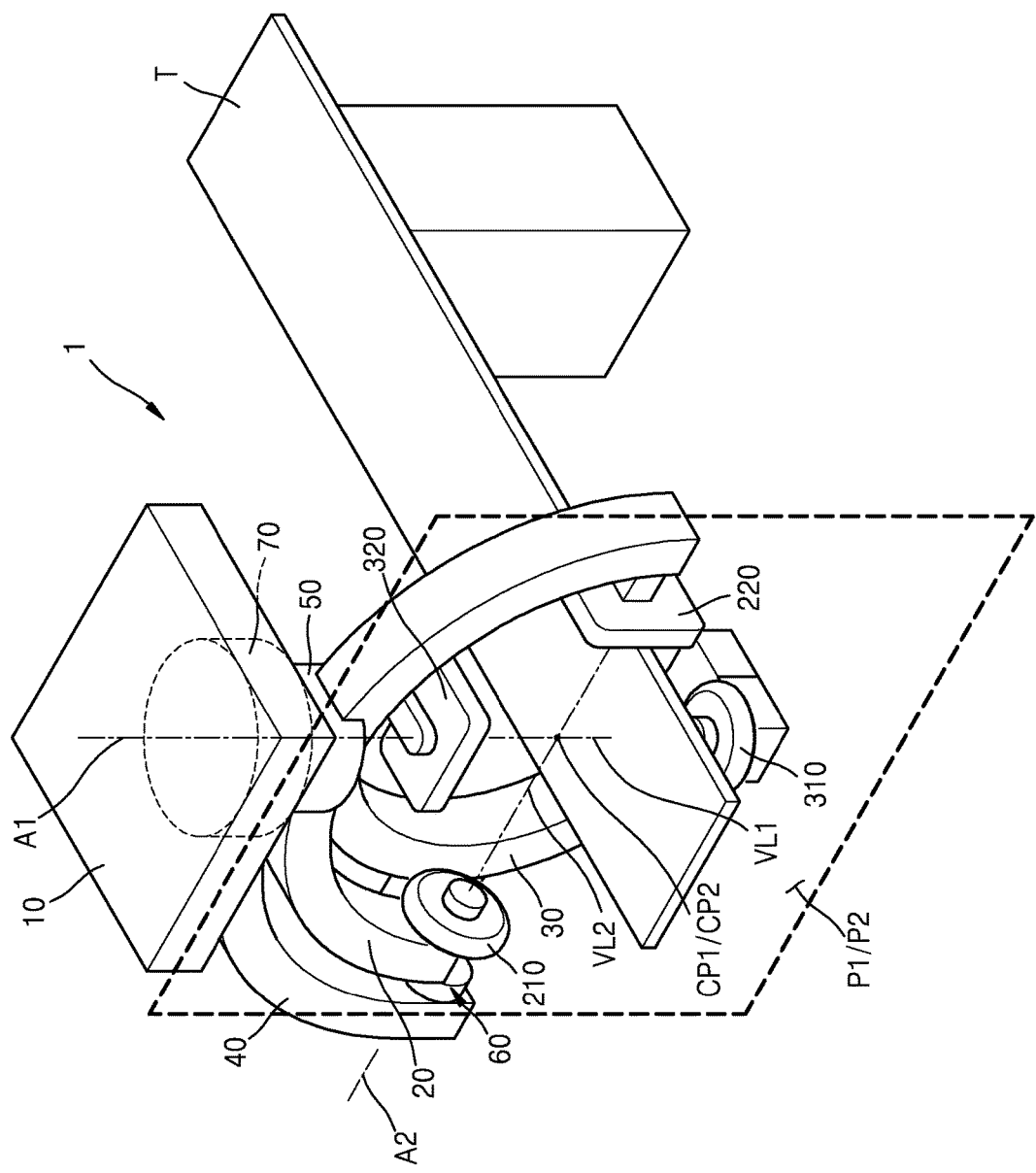
FIG. 5 is a perspective view of the radiation imaging apparatus in FIG. 1, in the case that a supporting arm is in a 90 degree rotation state.
Figure 6A:
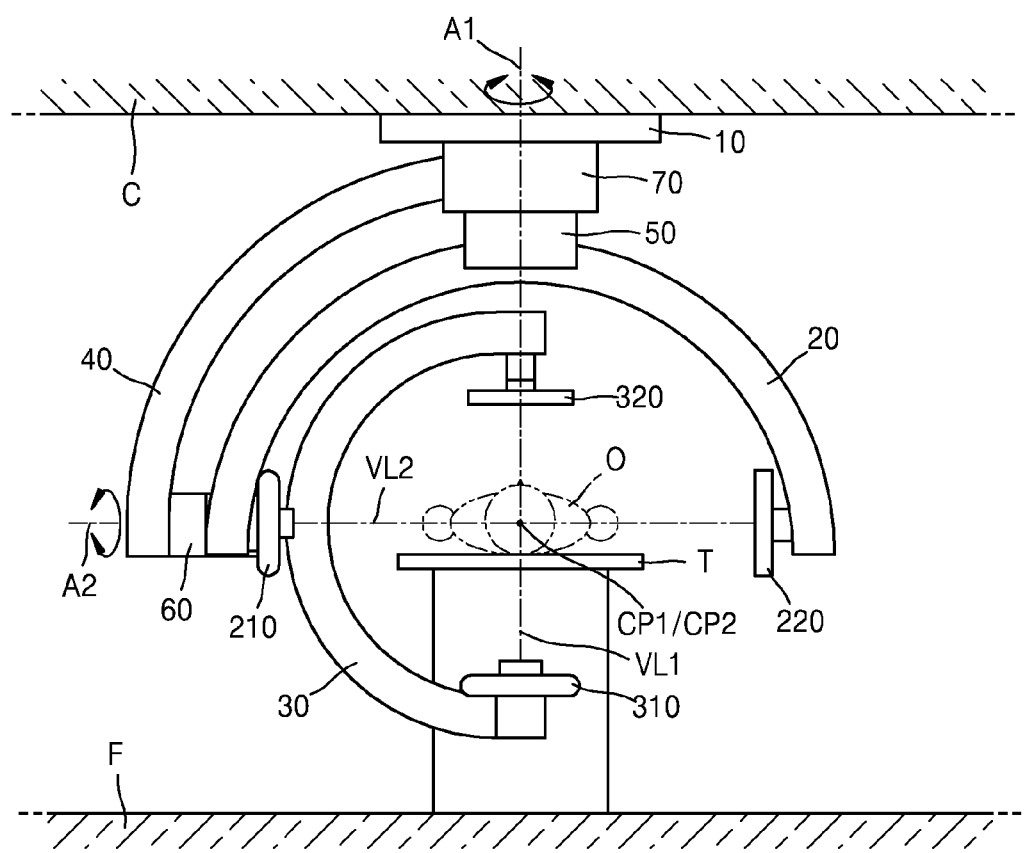
FIG. 6A and FIG. 6B are each a front view and a side view of the radiation imaging apparatus in FIG. 5.

FIG. 5 is a perspective view of the radiation imaging apparatus 1 in FIG. 1, in the case that the supporting arm 40 rotated 90 degrees with respect to FIG. 1. FIG. 6A is a front view and FIG. 6B is a side view of the radiation imaging apparatus 1 in FIG. 5.

Figure 6B:
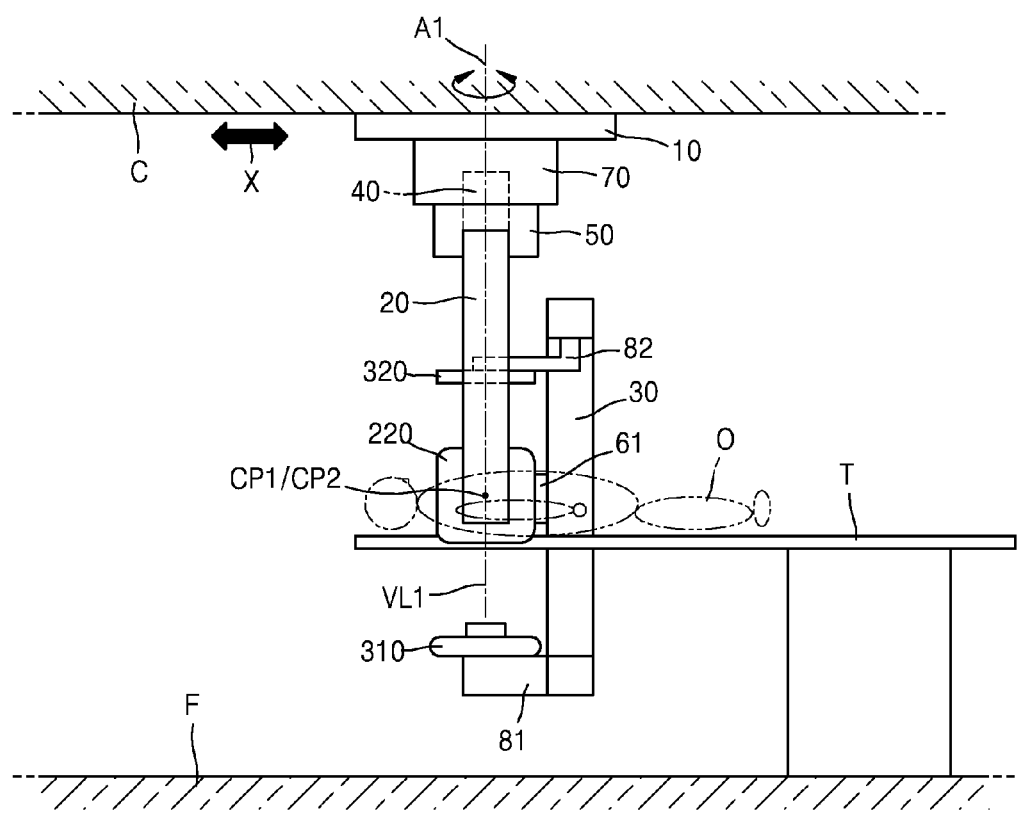

Referring to FIGS. 5, 6A, and 6B, the second radiation source 310 and the second radiation detector 320 may be on the second plane P2 defined by the virtual line VL2 connecting the first radiation source 210 to the first radiation detector 220 and the first rotation axis A1. The first plane P1 defined by the virtual line VL1 connecting the second radiation source 310 and the second radiation detector 320 and the second rotation axis A2. The first plane P1 and the second plane P2 may coincide.

The first arm 20 may be on the second plane P2. However, since the second arm 30 may be spaced apart from the first plane P1 as described above, even when the first arm 20 and the second arm 30 rotates such that the first plane P1 coincides with the second plane P2, an interference or collision of the first arm 20 and the second arm 30 does not occur. Referring back to FIGS. 2A and 2B, the size of the supporting arm 40, the size of first arm 20, and the size of second arm 30 may be different from one another. For example, an external radius R2 of the second arm 30 may be less than an internal radius R1 in of the first arm 20. An external radius R1 out of the first arm 20 may be less than an internal radius R3 of the supporting arm 40. Accordingly, when at least one of the first and second arms 20 and 30 and the supporting arm 40 rotates, the occurrence of interference with one another may be prevented or reduced.

Figure 7:
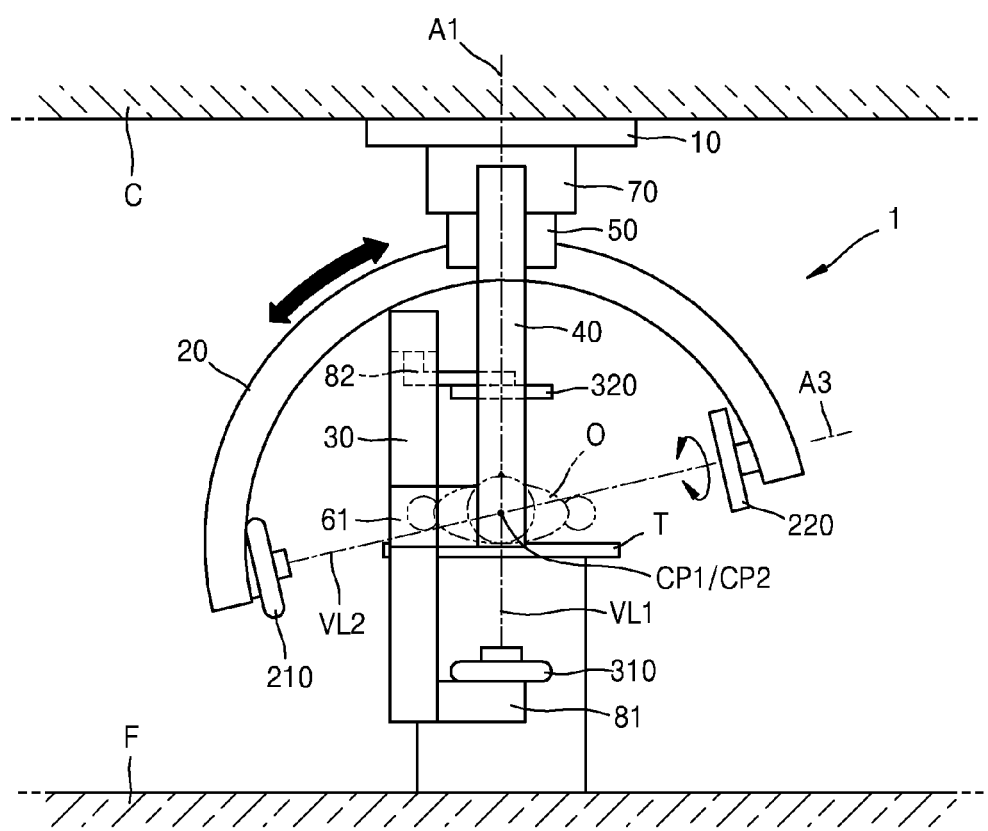
FIG. 7, FIG. 8 and FIG. 9 are views illustrating in the case that the degree of freedom of radiation imaging apparatus 1 is increased.
Figure 8:
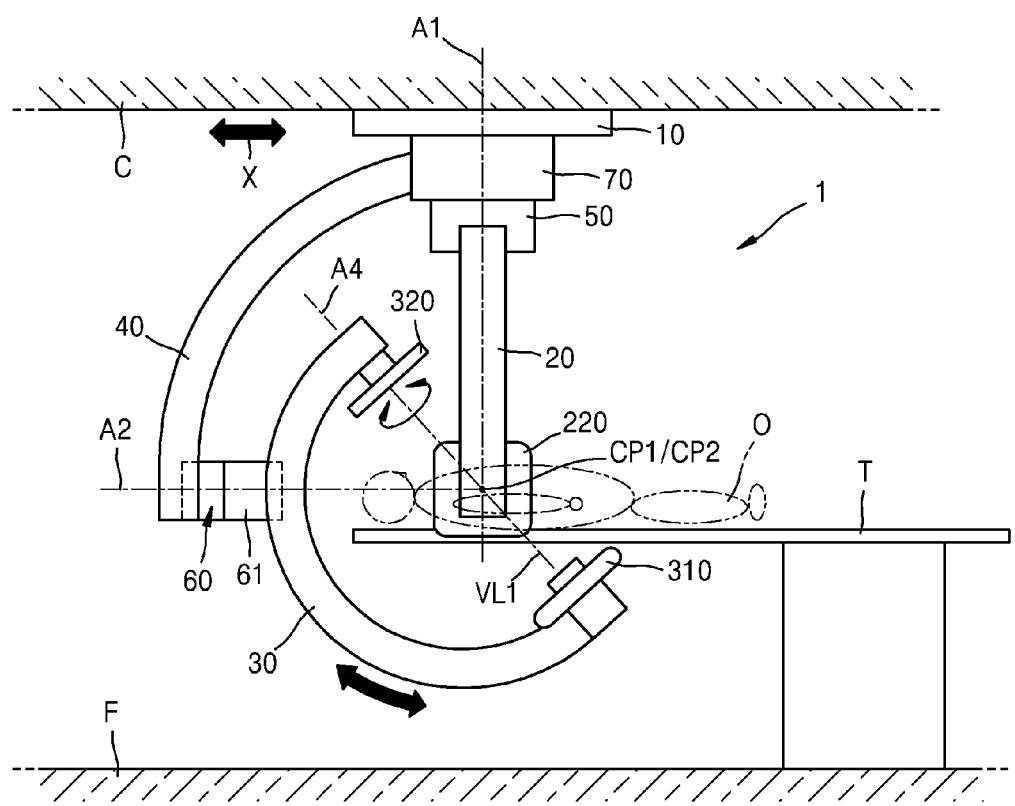
Figure 9:
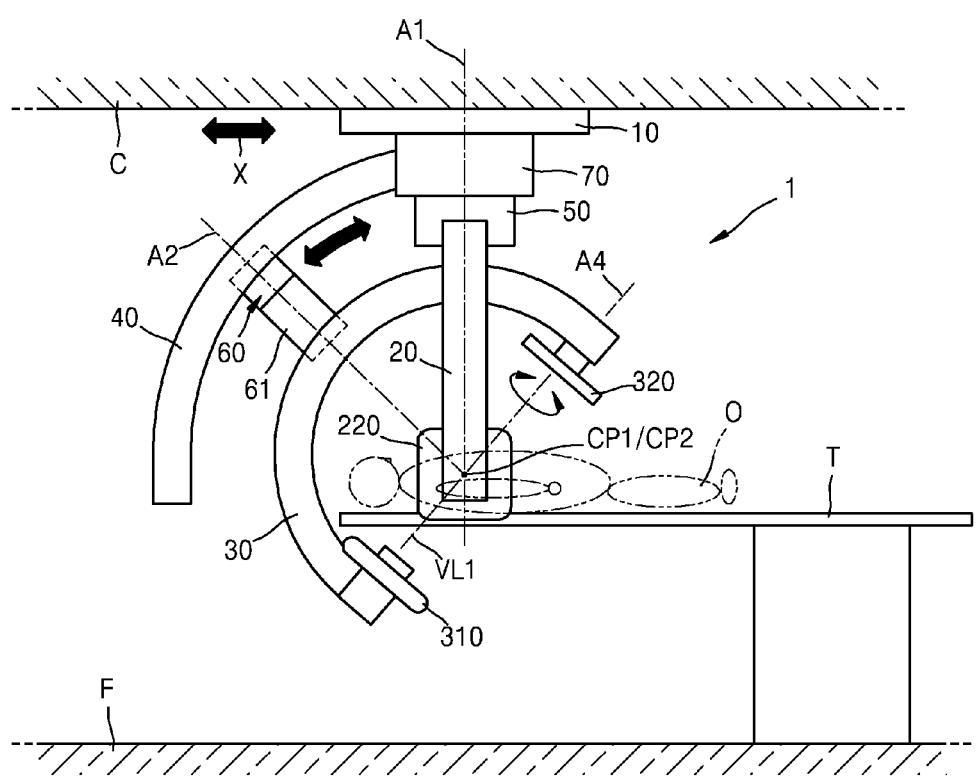

The radiation imaging apparatus 1 according to an embodiment is now described above in light of a structure having 4 degrees of freedom in that the moving member 10 may move along the ceiling C, the first arm 20 and supporting arm 40 may rotate with respect to the first rotation axis A1, and the second arm 30 may rotate with respect to the second rotation axis A2. However, the degree of freedom of the radiation imaging apparatus 1 is not limited thereto, and may increase or decrease. FIGS. 7 to 9 are views illustrating additional degrees of freedom for the radiation imaging apparatus 1. Referring to FIGS. 7 to 9, the moving member 10 may move along the ceiling C, the first arm 20 and supporting arm 40 may rotate with respect to the first rotation axis A1, and the second arm 30 may rotate with respect to the second rotation axis A2 in the radiation imaging apparatus 1. The description therefor is the same as described above, the description therefor will not be repeated.

Referring to FIG. 7, the first arm 20 may be slid along the first rotation member 50. The first arm 20 may be arc shaped. While the first arm 20 is sliding about the first rotation member 50, the first radiation source 210 and the first radiation detector 220 provided on the first arm 20 may rotate with respect to the first intersection point CP1. In addition, the first radiation detector 220 may rotate with respect to a third rotation axis A3 about the first arm 20.

Referring to FIG. 8, the second arm 30 may be slid along the second rotation member 60. The second arm 30 may be arc shaped. While the second arm 30 is sliding about the second rotation member 60, the second radiation source 310 and the second radiation detector 320 provided on the second arm 30 may rotate with respect to the first intersection point CP1. In addition, the second radiation detector 320 may rotate with respect to a fourth rotation axis A4 about the second arm 30.

Referring to FIG. 9, the second rotation member 60 may slide along the supporting arm 40. The supporting arm 40 may be arc shaped. While the second rotation member 60 is sliding along the supporting arm 40, the second arm 30 supported by the second rotation member 60 may move along the circumferential direction, accordingly, the second radiation source 310 and the second radiation detector 320 supported by the second arm 30 may rotate with respect to the first intersection point CP1.

In the radiation imaging apparatus 1 according to an exemplary embodiment, a radiation source and a radiation detector provided on either the first arm 20 or the second arm 30 may be simultaneously moved.

To aid in understanding the embodiments, reference numerals are used in the exemplary embodiments shown in the drawings, and specific terms are used to explain the exemplary embodiments; however, they are not intended to limit the embodiments and may represent all the components that could be considered by those skilled in the art.

Specific executions described herein are merely examples and do not limit the scope of the embodiments in any way. For simplicity of description, other functional aspects of conventional electronic configurations, control systems, software and the systems may be omitted. Furthermore, line connections or connection members between elements depicted in the drawings represent functional connections and/or physical or circuit connections by way of example, and in actual applications, they may be replaced or embodied as various additional functional connection, physical connection or circuit connections. Also, the described elements may not be inevitably required elements for the application of the embodiments unless they are specifically mentioned as being "essential" or "critical." The term "include" or "comprise" used herein should not be interpreted to include all the various stages of the various components described in the specification, or the components some of them or some of these steps It should be understood that the exemplary embodiments described therein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope thereof as defined by the following claims.

What is claimed is:

1. A radiation imaging apparatus comprising:
a moving member configured to move along a ceiling;
a first arm supported by the moving member to rotate with respect to a first rotation axis, wherein the first arm supports a first radiation source and a first radiation detector which are facing each other;
a second arm configured to rotate with respect to a second rotation axis crossing the first rotation axis, wherein the second arm supports a second radiation source and a second radiation detector which are facing each other; and
a supporting arm supported by the moving member, wherein the supporting arm supports the second arm such that the second arm is rotatable with respect to the second rotation axis,
wherein the second arm is supported by the supporting arm through a second rotation member which is rotatably connected to the supporting arm with respect to the second rotation axis, and
at least one of the first arm and the second arm is spaced apart from a plane defined by a virtual line connecting at least one of the first radiation source and the second radiation source to at least one of the first radiation detector and the second radiation detector supported by the at least one arm and at least one of the first rotation axis and the second rotation axis of the at least one arm.

2. The radiation imaging apparatus of claim 1, wherein the supporting arm is supported by the moving member to rotate with respect to the first rotation axis.

3. The radiation imaging apparatus of claim 1, wherein the second arm is spaced apart from the plane defined by the virtual line connecting the second radiation source to the second radiation detector and the second rotation axis.

4. The radiation imaging apparatus of claim 1, wherein a point where the first rotation axis and the second rotation axis intersect corresponds to a point where a virtual line connecting the first radiation source to the first radiation detector and the virtual line connecting the second radiation source to the second radiation detector intersect.

5. The radiation imaging apparatus of claim 1, wherein each of the first and second arms is arc shaped.

6. The radiation imaging apparatus of claim 5, wherein the first arm is supported by the moving member through a first rotation member rotatably connected to the moving member.

7. The radiation imaging apparatus of claim 6, wherein the first arm is configured to slide along the first rotation member.

8. The radiation imaging apparatus of claim 6, wherein the second arm is configured to slide along the second rotation member.

9. The radiation imaging apparatus of claim 6, wherein the supporting arm is arc shaped, and the second rotation member is configured to slide along the supporting arm.

10. The radiation imaging apparatus of claim 1, wherein the first rotation axis is orthogonal to a movement direction of the moving member.

11. The radiation imaging apparatus of claim 1, wherein the moving member is configured to move along a length direction of an examination table.

12. The radiation imaging apparatus of claim 1, wherein the first radiation source and the second radiation source are configured to transmit a selected one from a group consisting of X-rays, ultrasound, magnetic fields, and pulses of radio wave energy.

* * * * *